United States Patent [19]
NessAiver et al.

[11] Patent Number: 5,447,155
[45] Date of Patent: Sep. 5, 1995

[54] HIGH TEMPORAL RESOLUTION BLACK BLOOD CINE IMAGING

[75] Inventors: Moriel S. NessAiver, Cleveland Heights; James B. Murdoch, Solon, both of Ohio

[73] Assignee: Picker International, Inc., Highland Hts., Ohio

[21] Appl. No.: 859,153

[22] Filed: Mar. 27, 1992

Related U.S. Application Data

[63] Continuation-in-part of Ser. No. 791,855, Nov. 14, 1991, Pat. No. 5,273,040.

[51] Int. Cl.[6] .............................................. A61B 5/055
[52] U.S. Cl. ................................ 128/653.2; 128/653.3
[58] Field of Search ........................... 128/653.2, 653.3; 324/306, 309

[56] References Cited

U.S. PATENT DOCUMENTS

| | | | |
|---|---|---|---|
| 4,715,383 | 12/1987 | Ehman et al. | 128/653.2 |
| 4,782,839 | 11/1988 | Hennig et al. | 324/306 |
| 4,836,209 | 6/1989 | Nishimura | 324/306 |
| 4,849,697 | 7/1989 | Cline et al. | 324/306 |
| 5,031,624 | 7/1991 | Mistretta et al. | 324/306 |
| 5,034,694 | 7/1991 | Sattin et al. | 324/309 |
| 5,070,299 | 12/1991 | Kiefer et al. | 324/309 |
| 5,079,504 | 1/1992 | Machida | 324/309 |
| 5,159,550 | 10/1992 | Sakamoto et al. | 364/413.13 |
| 5,195,524 | 3/1993 | Takiguchi et al. | 128/653.3 |
| 5,199,435 | 4/1993 | Sugimoto et al. | 128/653.2 |
| 5,222,500 | 6/1993 | Sugimoto | 128/653.2 |
| 5,271,399 | 12/1993 | Listerud et al. | 128/653.3 |
| 5,307,014 | 4/1994 | Laub | 128/653.3 |

FOREIGN PATENT DOCUMENTS

4020938 1/1991 Germany ................. 128/653.2

*Primary Examiner*—Krista M. Zele
*Attorney, Agent, or Firm*—Fay, Sharpe, Beall, Fagan, Minnich & McKee

[57] ABSTRACT

During a cardiac cine examination, a multiplicity of imaging sequences, each about 20 msec long, are applied following the R-wave. Each imaging sequence includes a saturation portion in which a bi-modal pre-saturation pulse (38) and a spoiler gradient (56) are applied. The bi-modal RF pulse has a relatively low tip angle, about 50°, but is repeated sufficiently often that blood in regions (30a, 30b) parallel to a selected slice (32) are driven toward saturation. Each imaging sequence further includes a gradient echo or other conventional imaging sequence during an imaging portion to generate magnetic resonance data (60). Each imaging sequence is repeated twice for each temporal interval with the same phase encoding, but once with the relative phase of the signal in the slice and the relative phase of the signals from within the pair of regions (30a, 30b) reversed. These two signals are combined such that the signals from within the slice add and the signals from with the pair of regions subtract. Signals corresponding to the same temporal interval after the R-wave with each of a multiplicity of phase encodings are reconstructed (82) into an image representations (84) for display on a video monitor (96).

6 Claims, 6 Drawing Sheets

HIGH TEMPORAL RESOLUTION BLACK BLOOD CINE IMAGING

This application is a continuation-in-part of U.S. application Ser. No. 07/791,855, now U.S. Pat. No. 5,273,040, filed Nov. 14, 1991.

BACKGROUND OF THE INVENTION

The present invention relates to the art of magnetic resonance cine imaging. It finds particular application in conjunction with black blood cine imaging of the heart and will be described with particular reference thereto. It is to be appreciated, however, that the invention will also find application in conjunction with angiography, circulatory, and other examinations in which a flowing fluid is to be displayed dark.

Cine images have commonly been acquired using field echoes. Field echoes permit a rapid repetition rate, e.g. up to 64 sequence repetitions per second. In cardiac cine imaging, this enabled a view of data for each of 64 images to be collected in a single cardiac cycle. However, in the images from field echo sequences, the blood appears bright. The bright area of the image corresponding to blood tends to cause artifacts and ghosting. The problem of ghosting in gradient echo cine imaging is in part due to changes in the position of the heart due to respiration and cardiac beating from sequence repetition to sequence repetition.

An additional disadvantage of gradient echo imaging is a blurring of the interface between the heart tissue, and the blood. More specifically, a loss of contrast occurs between slow moving blood and the myocardium when the slow moving blood remains within the imaging plane long enough to become saturated. This typically occurs, but not exclusively, in the apex of the heart, making it difficult to determine myocardial mass, wall thickness, and chamber volumes accurately.

It is commonplace in angiography studies to saturate the blood tissue such that it appears dark in the resultant image. However, the saturation techniques used in angiography requires large RF pulses and large spoiler gradients. These large RF pulses and spoiling gradients not only require a large amount of power, but also require a relatively long duration. The duration needed to achieve saturation in angiography sequences with large spoilers is too long for effective cine examinations.

In a technique described in "Cineangiography of the Heart in a Single Breath Hold with Segmented Turbo-FLASH Sequence", Radiology, Vol. 178, pp. 357–360, Atkinson and Edelman (RSNA, 1991), limited pre-saturation was incorporated into a cine sequence. More specifically, the Atkinson and Edelman technique generated cine images along the long axis of the heart, i.e. generally vertically in a standing patient. This technique pre-saturated the atria to saturate blood flowing into the heart. This caused the blood in the resultant image to be dark during diastole when the saturated blood flowed in from the atria. However, during systole, when the heart is contracting and hence, in the most clinically interesting portion of its cycle, this technique results in blood that is neither bright nor dark. Rather, the blood is gray, very close in intensity to the gray scale of the surrounding myocardium. Thus, this technique does not provide good images for measuring cardiac volume during end diastole or end systole. Moreover, the pre-saturation causes a dark stripe to appear across the image, totally obliterating the signal from the atria.

Another disadvantage of the Atkinson technique is that Atkinson uses very large spoiling gradients to prevent signal from the pre-saturation slab from interfering with the desired image. These large spoiler gradients significantly decrease temporal resolution, i.e. lengthen the sequence time.

Dark blood images can also be obtained using spin echo techniques. Spin echo cines are obtained by acquiring multiple acquisitions with varying delays after the R-wave. These acquisitions are then sorted and recombined based upon their temporal order. Although spin echo images generally have dark blood and show good anatomical detail, they suffer from a very low temporal resolution, typically 6–12 views per cardiac cycle. A one-frame image typically requires about 4 minutes and a six-frame cine would require more than 24 minutes. This is much slower than gradient echo cines in which 20–64 views can be acquired in as little as one minute.

Further, spin echo images of the heart also suffer from the same type of ghosting as gradient echo cines. The ghosting is particularly apparent during diastole when the blood is flowing more slowly or not at all, depending on the slice location.

The present invention contemplates a new and improved cine technique which overcomes the above-referenced problems and others to provide dark blood cine images with high temporal resolution.

SUMMARY OF THE INVENTION

In accordance with the present invention, slices or slabs which are parallel to a selected imaging slice are subject to a steady state or driven pre-saturation. A gradient echo or other sequence with good temporal resolution is applied to cause the generation of magnetic resonance information from the selected slice.

The sequence is repeated with the same phase encoding for each frame as in a preceding heart beat but with the phase of the signal from the heart reversed relative to the phase of the saturated slabs from the preceding sequence. The data from the two sequences are combined such that resonance signals from the slice add and the resonance signals from outside of the slice subtract.

The steady state pre-saturation is created using a bi-modal pulse to generate both pre-saturation slices or slabs with a single pulse within a few milliseconds. The bi-modal pulse has a relatively small flip angle, significantly under 90°.

A relatively small spoiler gradient is applied immediately after the bi-modal pulse. The spoiling gradient reduces, but does not eliminate the magnetic resonance signal contribution from the saturated regions. The reduction in the out-of-slice signal causes the out-of-slice signals to cancel better when the phase reversed resonance signals are combined.

In accordance with another aspect of the present invention, the pre-saturation pulses use a flip angle of about 40°–70°.

In accordance with another more limited aspect of the present invention, a reduced refocusing excitation pulse is applied concurrently with the slice select gradient for defining thin slices.

One advantage of the present invention is that it eliminates the blood signal almost entirely. It also removes the ghosting typically found in bright blood cine and spin echo images.

Another advantage of the present invention resides in its improved temporal resolution. A 40 frame black blood cine can be acquired with a 4 minute acquisition time as compared to about a half hour acquisition time for 6 frames of spin echo images.

Another advantage of the present invention is that dark blood images are provided throughout the complete cardiac cycle, not just during diastole.

Another advantage of the present invention is its reduced power requirements due to small flip angles and small spoiling gradients.

Another advantage of the present invention resides in the improved diagnostic value of the resultant cine images.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1A:
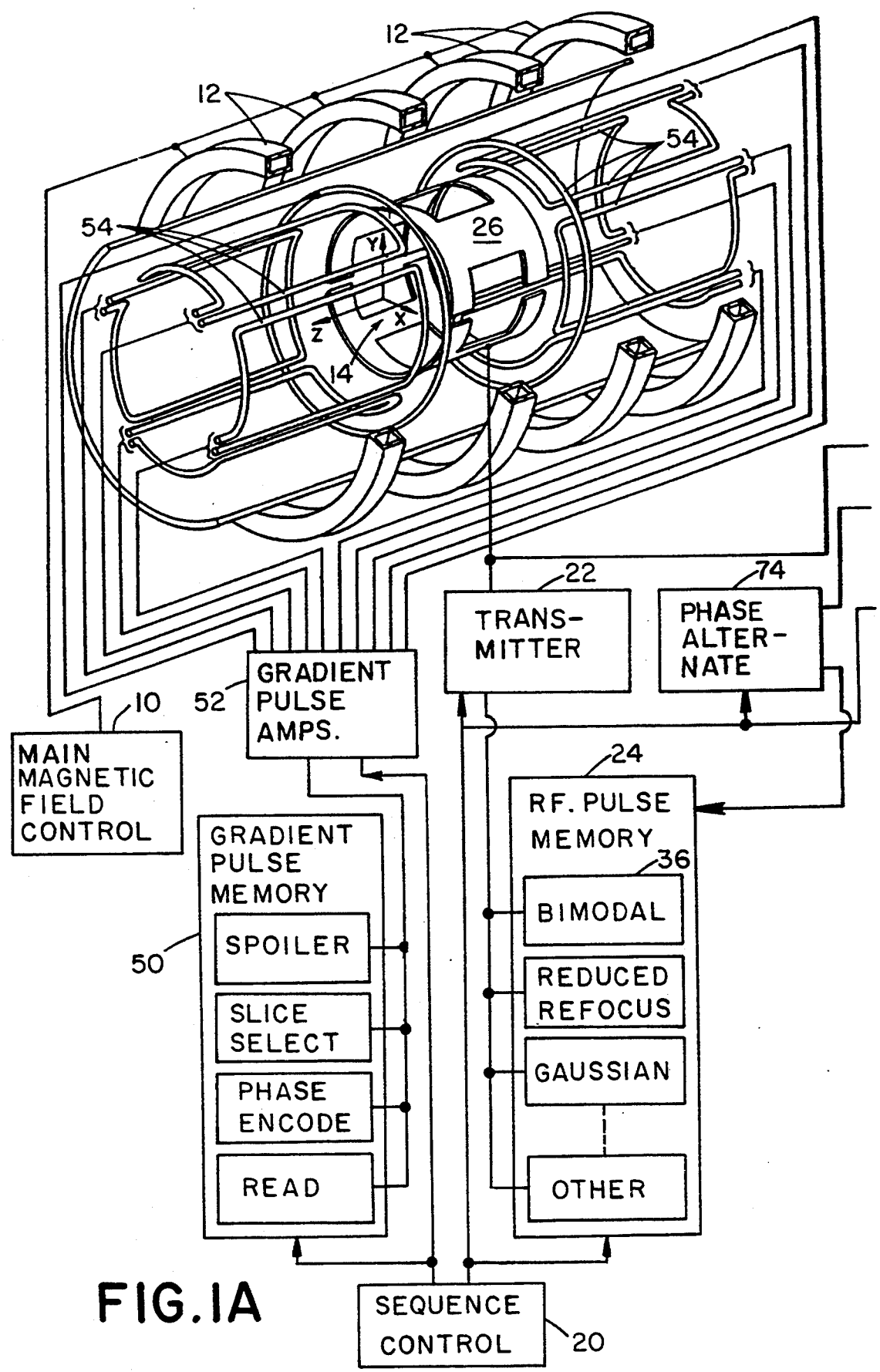
FIGS. 1A and 1B taken together are a diagrammatic illustration of a magnetic resonance imaging system in accordance with the present invention.
Figure 1B:
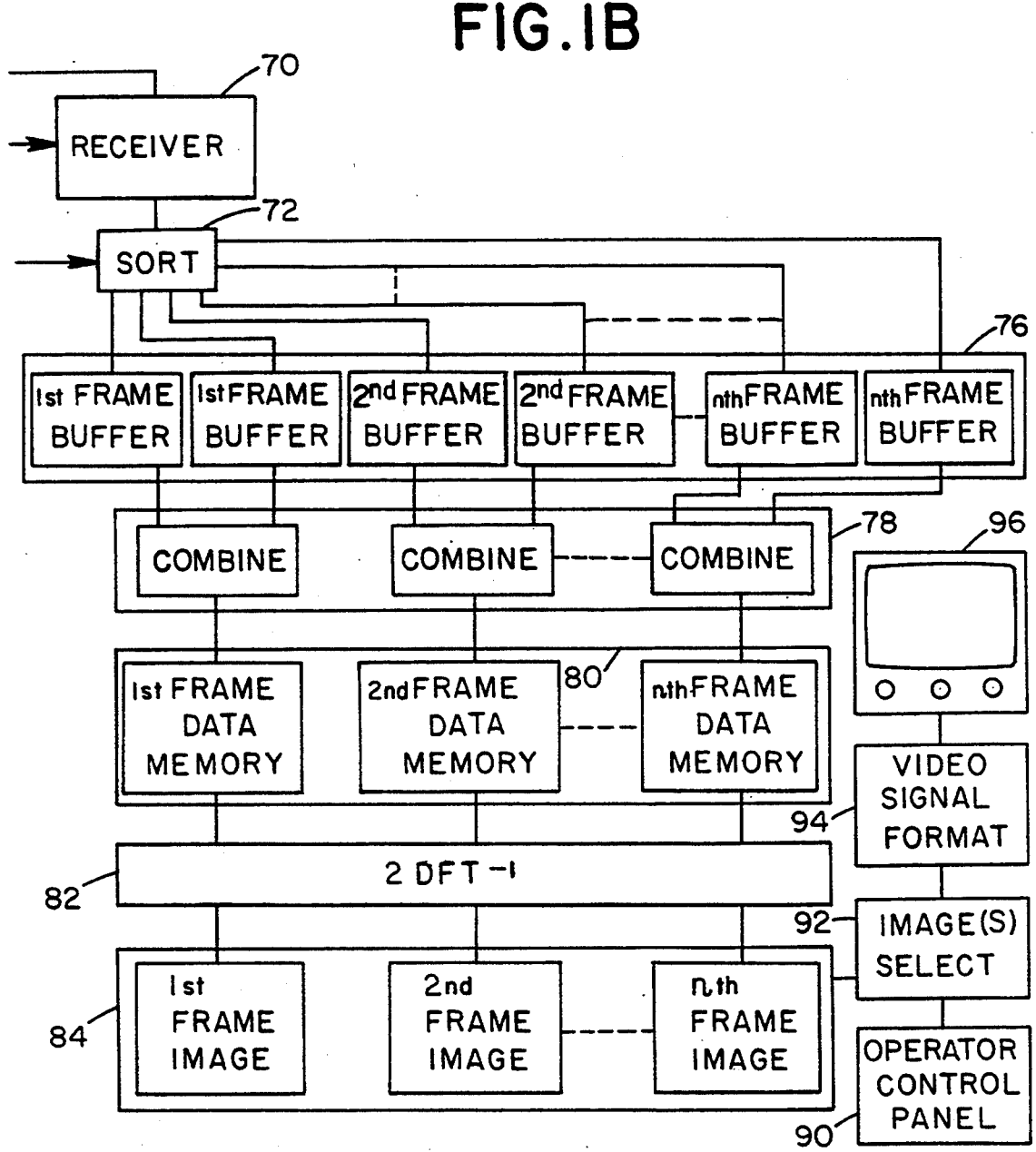

With reference to FIGS. 1A and 1B, a main magnet field control means 10 controls superconducting or resistive magnets 12 such that a substantially uniform main magnetic field is created longitudinally, along a z axis, through an examination region 14.

Figure 2:
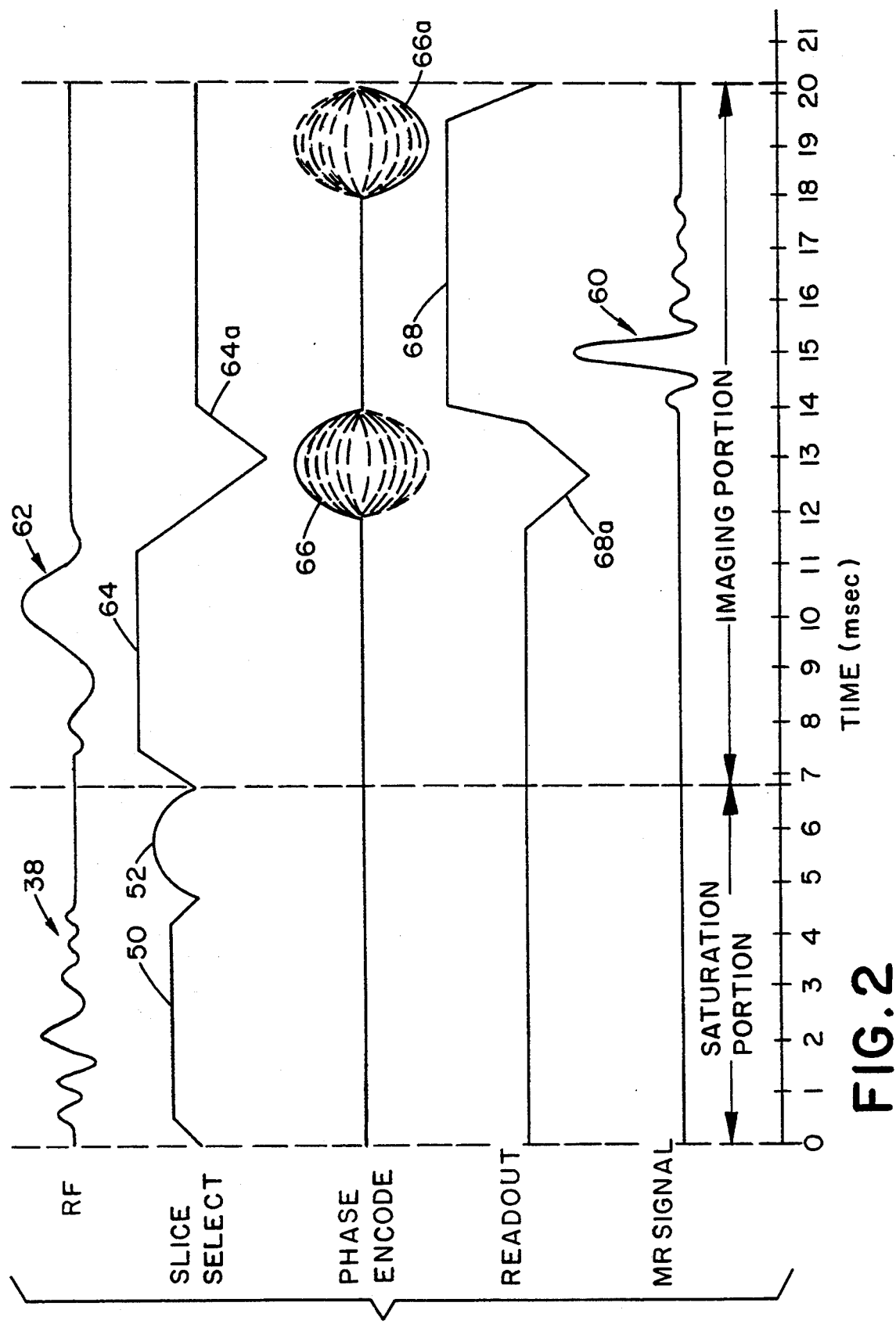
FIG. 2 illustrates a preferred pulse sequence in accordance with the present invention.
Figure 3:
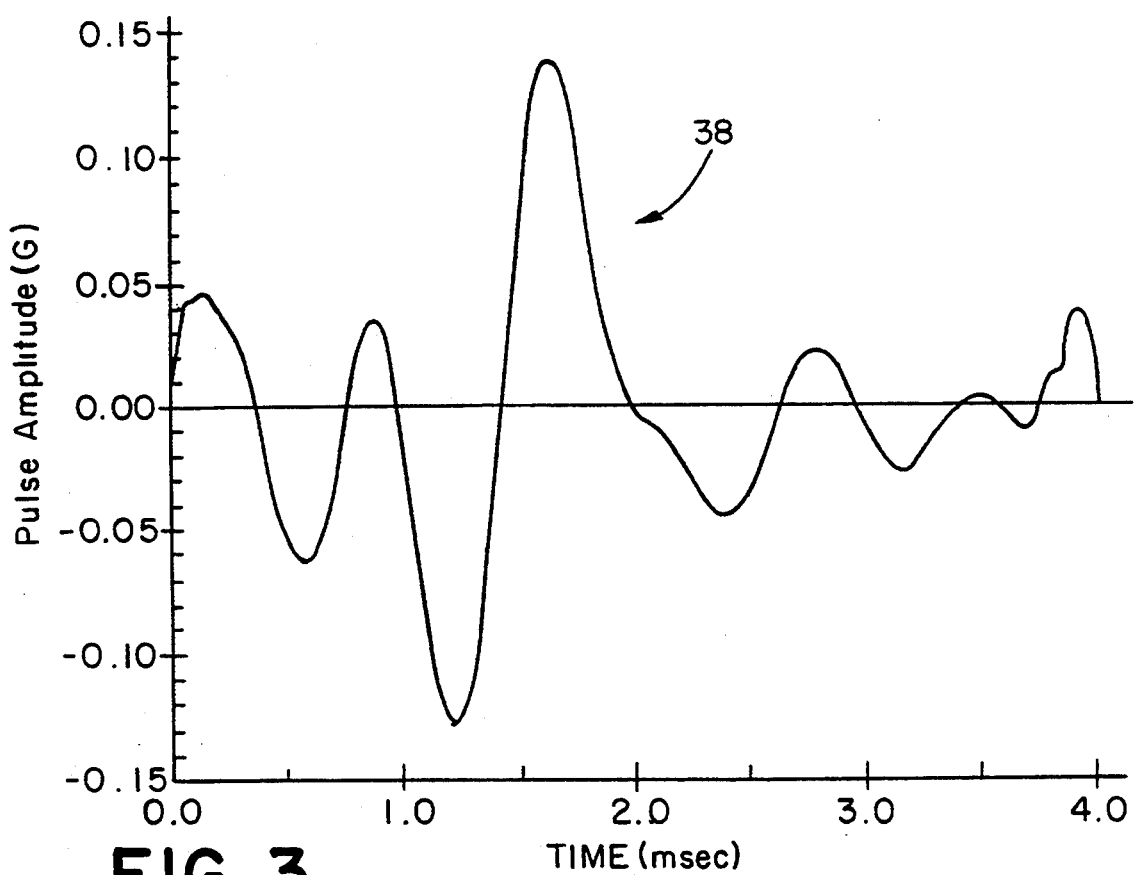
FIG. 3 is a detailed illustration of the pre-saturation pulse of FIG. 2.
Figure 4:
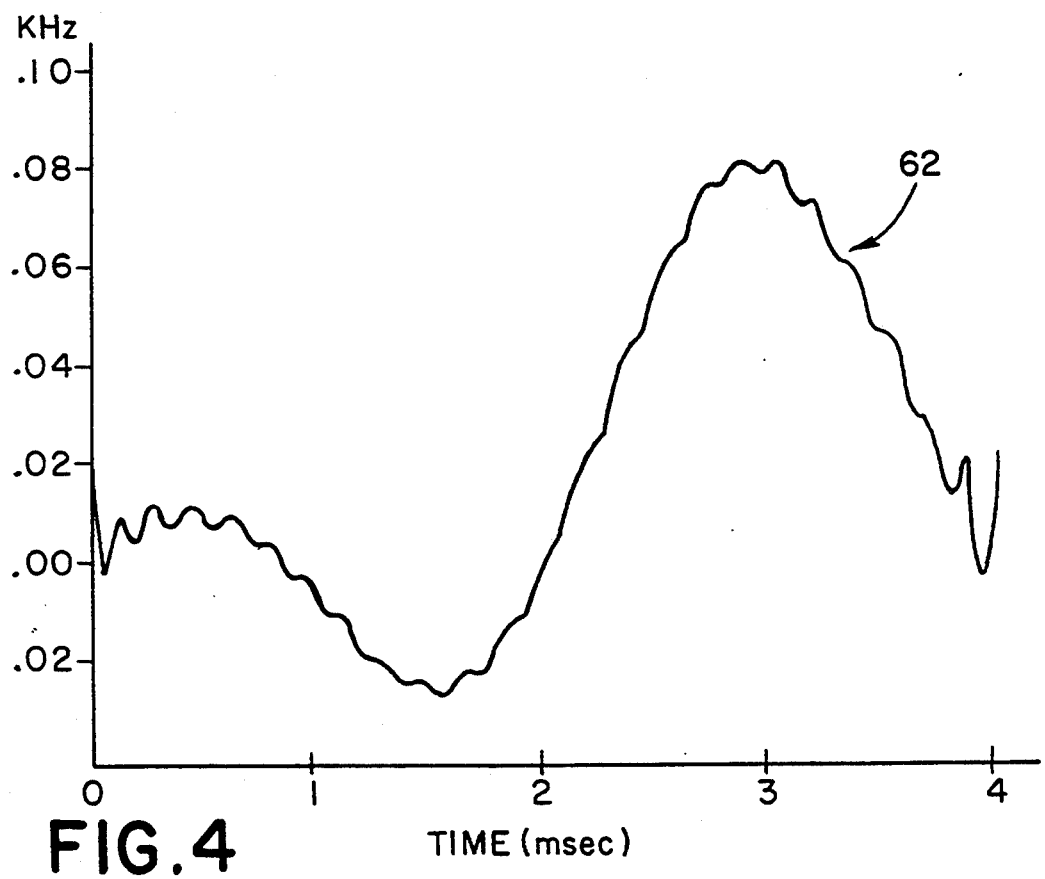
FIG. 4 is a detailed illustration of the preferred reduced refocusing excitation pulse of FIG. 2.

With continuing reference to FIGS. 1A and 1B and further reference to FIG. 2, a sequence control means 20 controls a radio-frequency transmitter 22 and an RF pulse memory or control means 24 to cause a series of RF pulses, such as those illustrated in FIGS. 2, 3, and 4 to be conveyed to an RF coil 26.

Figure 5:
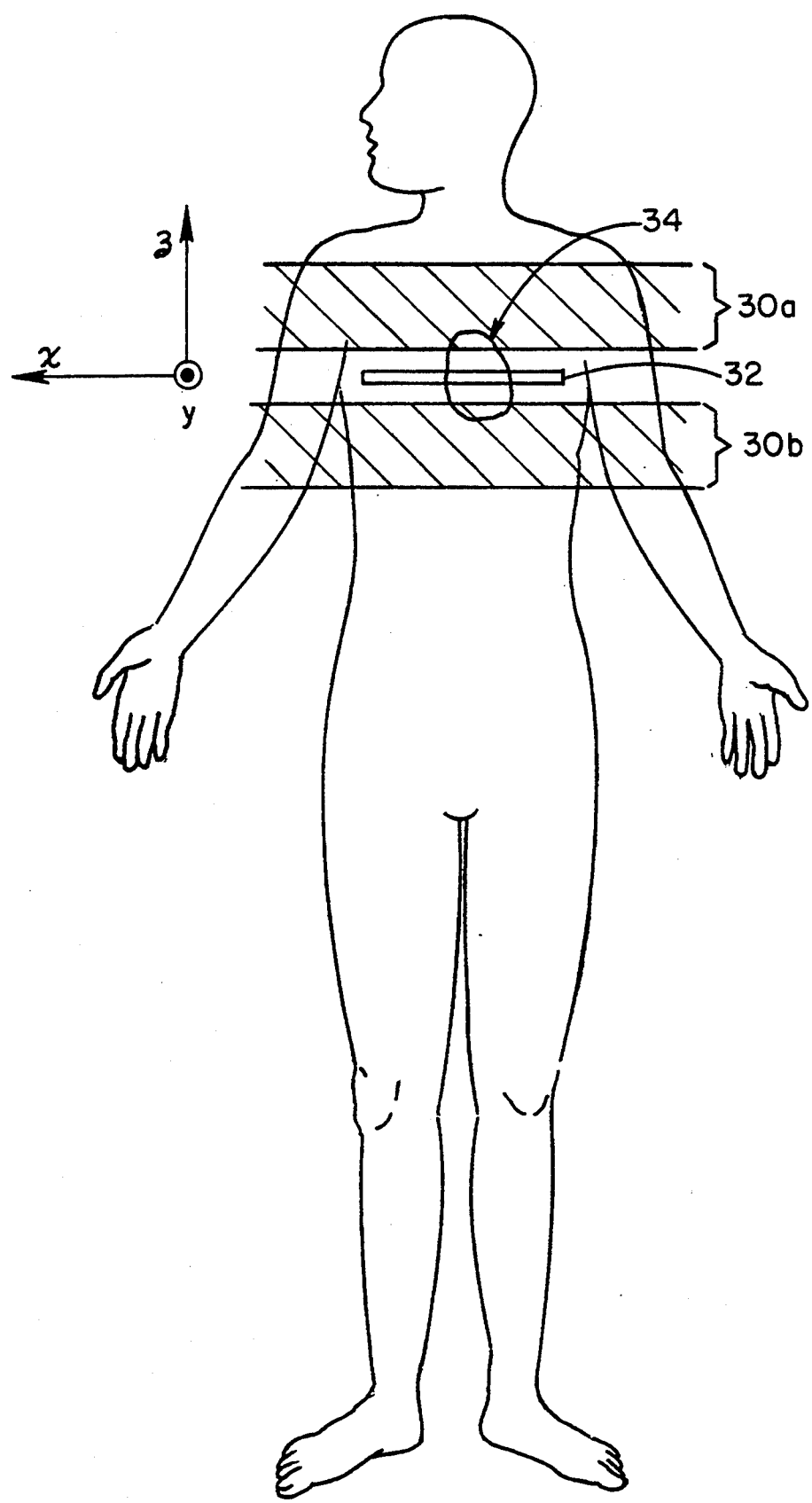
FIG. 5 is a diagrammatic illustration of the saturated slabs and imaging slice, superimposed on a patient.
Figure 6:
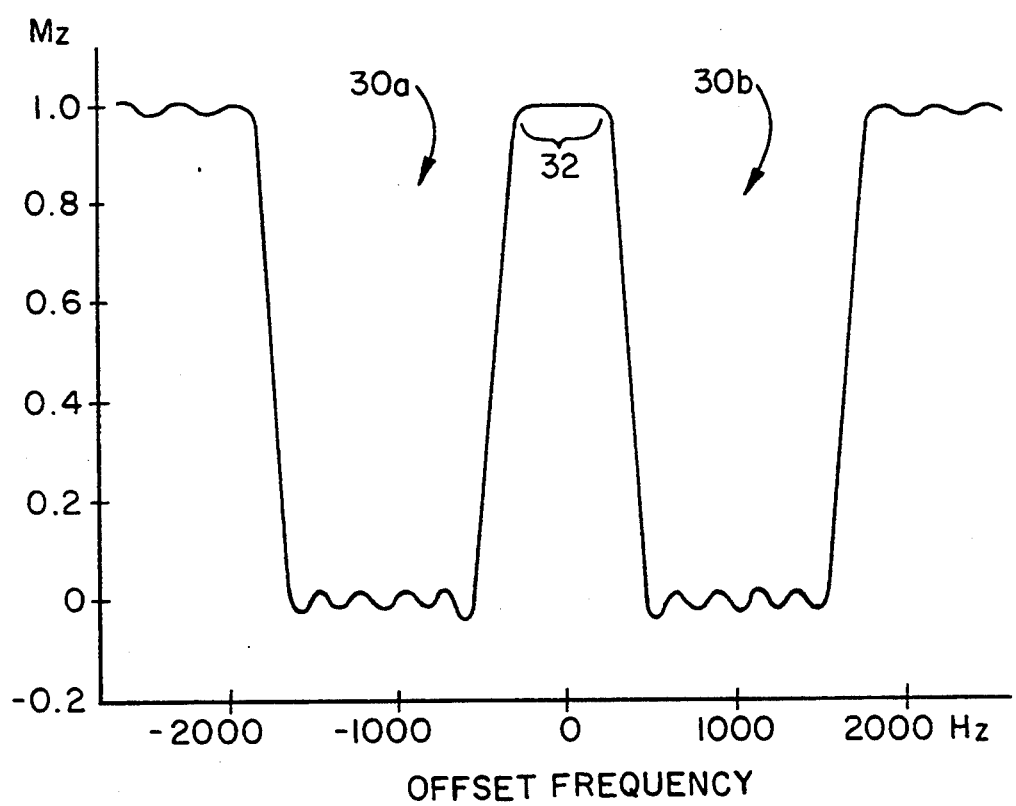
FIG. 6 illustrates the resultant saturation slice profile produced by the sequence of FIG. 3; and, FIG. 7 illustrates the slice profile achieved with the excitation pulse of FIG. 4.
Figure 7:
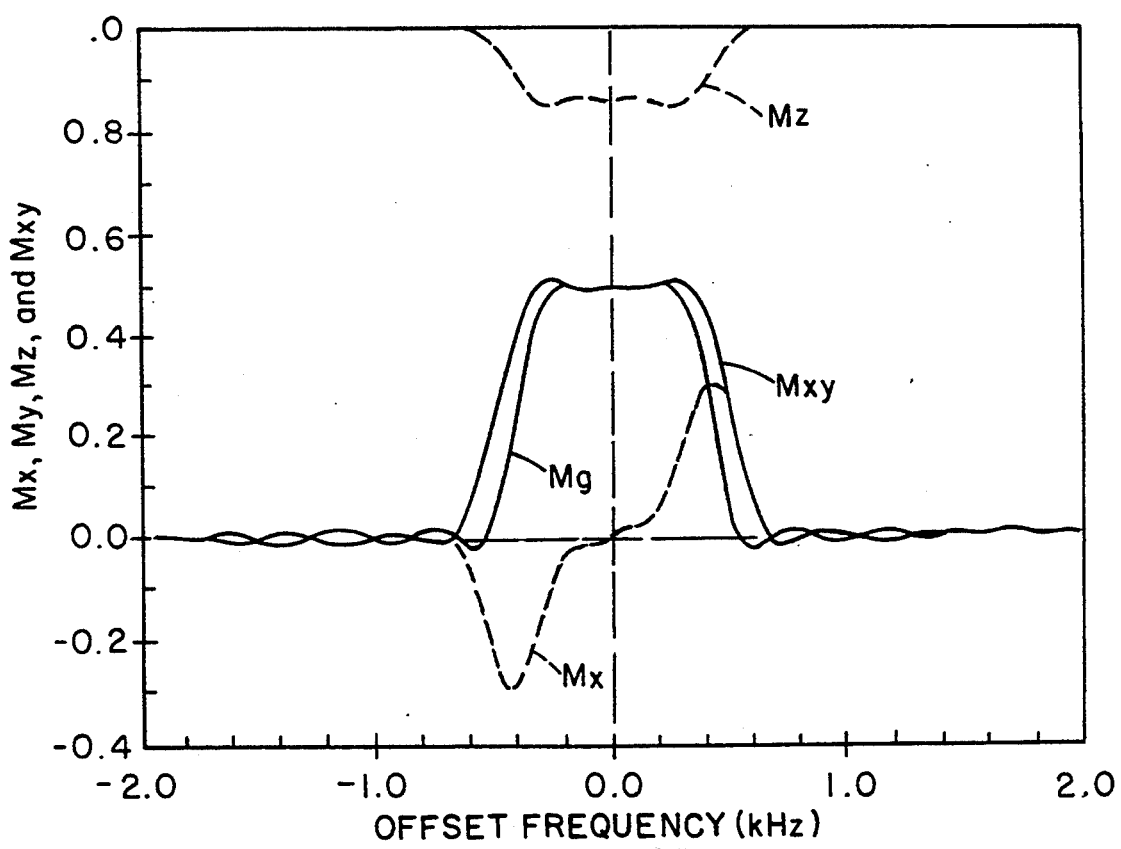

With continuing reference to FIGS. 1A, 1B, and 2 and further reference to FIGS. 5 and 6, a means is provided for driving blood in regions or slabs 30a and 30b toward steady-state pre-saturation. In the preferred embodiment, regions 30a and 30b are slabs about 6 cm thick, spaced about 4 or 5 cm apart in parallel with a selected imaging slice 32 of about 1 cm through a cardiac region 34 of a subject. More specifically, the saturation regions 30a and 30b are caused by the sequence control means 20 accessing a bi-modal out-of-slice saturation pulse memory portion 36 of the RF slice profile memory 24 to retrieve an RF pulse profile, preferably in the form of a digital word. The profile causes the transmitter 22, preferably a digital transmitter, to generate an RF pulse 38 of the configuration illustrated in FIG. 3. It is to be appreciated that the slice may be selected along the long, short, or other axis of the heart.

A gradient pulse control or memory 40 supplies gradient pulse shape information to gradient pulse amplifiers 42. The gradient pulse amplifiers apply current pulses of appropriate amplitude to gradient coils 44 to cause gradients of the configuration illustrated in FIG. 2 across the examination region 14.

More specifically, a means is provided for applying the bi-modal saturation pulse 38 and a saturation region slice select gradient 50 concurrently to cause the excitation profile of FIG. 6. The bi-modal saturation pulse and slice select gradient maximize linearity in a central region corresponding to the gap between the saturation regions 30a and 30b. The bi-modal saturation pulse rotates the magnetization in the saturation regions 30a and 30b with a flip angle of less than 70°, preferably 50°. Because this sequence is repeated very rapidly, about every 20 msec in the preferred embodiment, a 50° flip angle maintains a steady-state saturation of static tissue in regions 30a and 30b. Of course, new blood keeps flowing into regions 30a and 30b which needs to be driven to saturation, preferably over a few repetitions of the sequence. Regions 30a and 30b are sized such that substantially all blood requires the time of a sufficient number of sequence repetitions to cross the region that it becomes saturated before entering slice 32. The flip angle is increased for longer sequences and reduced for shorter sequences. The linearity of the slice profile in regions 30a and 30b is not particularly significant because these regions are not being imaged.

After the bi-modal saturation and saturation slice select gradient pulses, a spoiler gradient 52 is applied in the slice select direction. In the preferred embodiment, the saturation slice select pulse 50 is about 4.5 msec long which determined by the duration of the bi-modal saturation pulse. The duration of the spoiler pulse is preferably about 2 msec. The amplitude of the spoiler pulse is reduced toward a level at which unacceptable image degradation and artifacting occurs. In the illustrated embodiment, the saturation portion of the sequence requires less than 7 msec.

Following the pre-saturation portion of the sequence during an imaging portion of the sequence, an image sequence means applies RF and gradient pulses which cause a magnetic resonance echo signal 60. More specifically to the preferred embodiment, the sequence control means 20 addresses the RF pulse memory 24 and the gradient pulse memory 50 to cause an RF excitation pulse 62 and a slice select gradient 64 to be applied concurrently. After resonance excitation in the selected slice 32, the slice select gradient has a rephasing portion 64a which is applied generally concurrently with a phase encode gradient 66 and a readout gradient dephasing portion 68a. The same phase encoding is applied in each of n repetitions of the sequence in a single cardiac cycle. The phase encoding is indexed at the beginning of a subsequent cardiac cycle to collect another view for each of n data sets each at a corresponding temporal interval after the R-wave or other selected point in the cardiac cycle.

After phase encoding, the read gradient is reversed, causing the magnetic resonance echo 60 concurrently with a read gradient 68. After the magnetic resonance signal 60, a phase unwinding gradient 66a is preferably applied, as necessary, to remove phase encoding artifacts. The saturation portion of the sequence for generating the magnetic resonance signal for the next temporal interval follows immediately. Alternately, for more rapid, less temporally resolved images, the phase encode gradient may be indexed in each of a subset of contiguous sequences and the resultant data used to generate a single, temporally less precious image.

The magnetic resonance signal is conveyed to a radio frequency receiver 70, preferably a digital receiver. The output of the digital receiver is conveyed to a sorting means 72 which sorts each received magnetic resonance signal by its temporal interval or frame. A phase alternating means 74 causes the phase of the radio frequency excitation pulse 62 and the receiver 70 to be reversed in alternate views with the same phase encoding corresponding to the same frame, i.e. the same temporal interval after the R-wave. The views from two sequential cardiac cycles which correspond to the same frame, but with the phase reversed, are conveyed to corresponding buffer memories or latches of an array 76. Pairs of buffers corresponding to the same frame are connected with one of an array of combining means 78. The combining means combine the phase alternated views such that signals from the selected slice 32 add and the out-of-slice signals, particularly signals from the saturation regions 30a and 30b, subtract or cancel.

The phase alternated averaged views are stored on a frame by frame basis in a data memory means 80. When a complete set of data corresponding to each frame has been generated over a series of cardiac cycles, a two-dimensional inverse Fourier transform or other magnetic resonance image reconstruction means 82 reconstructs each set of data into an image representation which is stored in an image array memory means 84.

An operator uses an operator console or control means 90 to cause a frame or image selection means 92 to select one or a series of the image representations from the image memory means 84. A video formatting means 94 formats the selected image data into an appropriate video or other signal for a video monitor 96 or other human-readable display. A series of n frames, e.g. 40 images representing the same slice in 20 msec. intervals, can be displayed in succession to show the beating of the heart. Other display modes, such as a stationary display of end diastole and end systole, are also commonly selected.

In this manner, a pre-saturation portion of the sequence which is less than 7 msec long saturates blood in regions 30a and 30b with limited spoiling. The regions 30a and 30b are sufficiently far apart that normal respiratory and cardiac movement do not shift portions of the cardiac tissue between the saturation regions and the image slice 32. The pre-saturation portion of the sequence is followed by an imaging sequence of 7 to 15 msec in duration. This enables a view to be collected every 17 to 22 msec. For a person with a heart rate of 60 beats/minute and an interbeat interval of 1000 msec, about 40 views per cardiac cycle can be collected by repeating the sequence of FIG. 2 forty times. In the next cardiac cycle, the phase is reversed and the same sequence is repeated. In the next subsequent cardiac cycle, the phase encode gradient 66 is incremented and the series of sequences repeated again, and so forth.

Although the slice 32 in FIG. 5 is illustrated as being taken transversely across the patient, it is to be appreciated that the present technique is applicable to slices in other directions as well. For slices taken through the major dimension of the heart, i.e. generally longitudinally relative to the patient, very thin slices are preferable. For thin, long dimension slices, the saturation regions 30a and 30b are moved closer together, as close as 1.5 to 2 cm, as very thin slices are advantageous to assure that sufficient blood is in the saturation regions 30a and 30b. In the longitudinal direction, a 5 to 6 mm slice is preferred as opposed to the more customary 10 mm slice in the transverse or short axis direction.

To achieve the narrow slice, a reduced refocusing excitation pulse of the shape shown in detail in FIG. 4 is preferred to achieve a narrow slice profile along the x, y, and z axes and in the x,y plane as illustrated in FIG. 6. Gaussian and other RF waveforms can also be used successfully, particularly for 1 cm and thicker slices.

Of course, other echo type sequences may also be utilized in the imaging portions including spin echo sequences. When shorter imaging sequence portions are used, the pre-saturation portions become closer together, allowing yet smaller flip angles to be used for saturation. Conversely, when longer imaging sequence portions are used, it may be necessary to increase the tip angle of the bi-modal pre-saturation pulse. As another alternative, two or another plurality of imaging portions may follow each saturation portion. However, the increase in duration between saturation portions requires larger flip angles on the bi-modal pre-saturation pulse.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A cardiac cine magnetic resonance method comprising:
   (a) selecting a slice through a subject to be imaged;
   (b) applying a bi-modal, pre-saturation RF pulse with a flip angle less than 70° concurrently with a pre-saturation slice select gradient to drive tissue in a pair of regions on either side of, parallel with, and displaced from the selected slice toward saturation;
   (c) after applying the bi-model, presaturation RF pulse, applying a spoiling gradient pulse along a slice select direction such that the bi-modal pre-saturation RF pulse and the spoiling gradient pulse taken together have a duration of less than 15 msec.;
   (d) following the spoiling gradient pulse, applying an imaging sequence portion including applying an imaging RF pulse to generate magnetic resonance signals;
   (e) repeating steps (b), (c), and (d) a multiplicity of times in such a manner that the bi-modal pre-saturation RF pulse drives the tissue in the pair of regions toward steady-state saturation;
   (f) repeating step (e) with each of a plurality of phase encodings;
   (g) reconstructing a plurality of image representations from temporally corresponding magnetic resonance signals generated in steps (d), (e), and (f).

2. The method as set forth in claim 1 wherein the flip angle of the pre-saturation RF pulse is 50° or less.

3. The method as set forth in claim 1 wherein the imaging sequence portion includes a gradient echo imaging sequence.

4. The method as set forth in claim 3 wherein steps (b) and (c) have a duration less than 7 msec and steps (b) through (d) taken together have a duration less than 22 msec.

5. A cardiac cine magnetic resonance method comprising:
   (a) selecting a slice through a subject to be imaged;
   (b) applying a bi-modal pre-saturation RF pulse with a flip angle less than 70° concurrently with a pre-saturation slice select gradient to drive tissue in a pair of regions on either side of, parallel with, and displaced from the selected slice toward saturation;
   (c) applying a spoiling gradient pulse along a slice select direction after the less than 70° flip angle pre-saturation RF pulse such that the pre-saturation RF pulse and the spoiling gradient pulse taken together have a duration of less than 15 msec.;
   (d) following the spoiling gradient pulse, applying an imaging sequence portion to generate magnetic resonance signals;
   (e) repeating steps (b), (c), and (d) a multiplicity of times such that flowing tissue in the pair of regions displaced from the selected slice is driven to steady-state saturation;
   (f) repeating step (e) with a phase reversal to reverse polarity of the magnetic resonance signals and combining corresponding magnetic resonance signals with opposite polarity;
   (g) repeating steps (e) and (f) with each of a plurality of phase encodings;
   (h) reconstructing a plurality of image representations from temporally corresponding magnetic resonance signals generated in steps (e), (f), and (g).

6. A cardiac cine magnetic resonance imaging apparatus comprising:
   a means for generating a static magnetic field through an examination region through a patient;
   a means for concurrently applying a pre-saturation slice select gradient and a bi-modal RF pulse with a flip angle less than 70° to the examination region for driving at least blood in a pair of regions disposed parallel to and displaced by an intervening thickness to either side of a selected slice toward saturation;
   a means for applying a spoiler gradient along a slice select axis after the bi-modal RF pulse such that the bi-modal RF pulse and the spoiler gradient taken together have a duration of less than 15 msec.;
   a means for concurrently applying an RF excitation pulse and an imaging slice select gradient along the slice select axis;
   a means for applying a phase encode gradient along a phase encode axis orthogonal to the slice select axis;
   a means for applying a read gradient along a read gradient axis orthogonal to the slice select and phase encode axes concurrently with a monitored magnetic resonance signal; the bi-modal RF pulse, the pre-saturation slice select gradient, the spoiler gradient, the RF excitation pulse, the imaging slice select gradient, and the phase encode gradient being applied a multiplicity of times following a preselected point in each cardiac cycle, such that a multiplicity of magnetic resonance signals are generated, each at a unique temporal duration after the preselected point of the cardiac cycle;
   a receiver for receiving the magnetic resonance signals;
   a means for combining magnetic resonance signals from corresponding temporal intervals after the preselected point in the cardiac cycle in such a manner that magnetic resonance signal contributions from within the slice sum and from outside the slice cancel;
   a means for reconstructing magnetic resonance data corresponding to each temporal interval into a corresponding image representation of the selected slice such that a plurality of time displaced images of the selected slice at differing points in the cardiac cycle are generated.

* * * * *